United States Patent [19]
Dombrowski et al.

[11] Patent Number: 5,279,570
[45] Date of Patent: Jan. 18, 1994

[54] NEEDLE ASSEMBLY WITH A MOVABLE STYLET CONTROLLED BY A SPACER MECHANISM

[75] Inventors: Mitchell P. Dombrowski, Grosse Pointe Farms; Mark I. Evans, West Bloomfield, both of Mich.

[73] Assignee: Wayne State University, Detroit, Mich.

[21] Appl. No.: 949,455

[22] Filed: Sep. 22, 1992

[51] Int. Cl.⁵ .............................. A01M 5/178
[52] U.S. Cl. ........................... 604/164; 604/165; 604/264; 606/125
[58] Field of Search ............ 604/164, 166, 165, 239, 604/264; 128/753, 754, 760, 749; 606/125, 184, 171, 151

[56] References Cited

U.S. PATENT DOCUMENTS

| | | | |
|---|---|---|---|
| 1,147,408 | 7/1915 | Kells | 604/164 |
| 1,248,492 | 12/1917 | Hill | 604/165 |
| 2,389,355 | 11/1945 | Goland et al. | 128/214 |
| 3,628,524 | 12/1971 | Jamshidi | 128/2 B |
| 4,308,875 | 1/1982 | Young | 128/753 |
| 4,713,057 | 12/1987 | Huttner et al. | 604/164 |
| 4,763,667 | 8/1988 | Manzo | 128/750 |
| 5,092,870 | 3/1992 | Mittermeier | 128/749 |
| 5,104,381 | 4/1992 | Gresh et al. | 604/164 |
| 5,163,947 | 11/1992 | Kvalo et al. | 128/749 |

Primary Examiner—John G. Weiss
Attorney, Agent, or Firm—Reising, Ethington, Barnard, Perry & Milton

[57] ABSTRACT

A needle assembly which comprises a hollow needle, a stylet, and a spacer mechanism to control the position of the stylet within the needle.

4 Claims, 2 Drawing Sheets

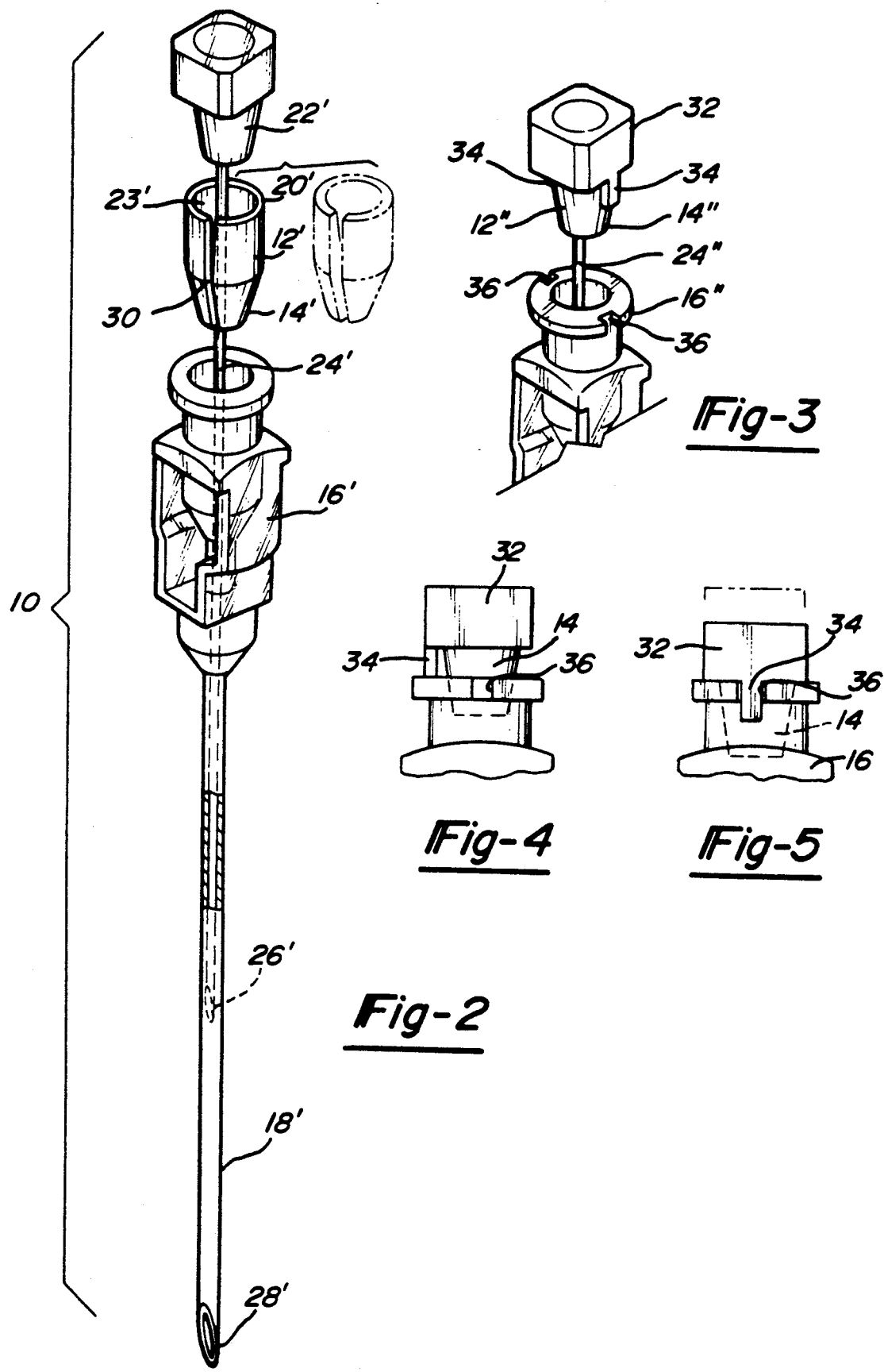

NEEDLE ASSEMBLY WITH A MOVABLE STYLET CONTROLLED BY A SPACER MECHANISM

FIELD OF INVENTION

The present invention relates to a needle assembly having a stylet which can be moved to project beyond the distal tip of the needle wherein the distance the stylet can be moved is controlled by a spacer mechanism.

BACKGROUND OF THE INVENTION

U.S. Pat. No. 4,763,667 (Manzo) issued Aug. 16, 1988, describes a tissue-penetrating catheter device useful in performing amniocentesis, having an inner catheter with a tissue-penetrating device, e.g., a needle, joined to the distal end of the inner catheter. The inner catheter is contained in an outer catheter and there is an element situated between the proximal ends of the inner and outer catheters which permits adjustment of the distance the tissue-penetrating device will extend.

U.S. Pat. No. 4,308,875 (Young) issued Jan. 5, 1982, describes an amniocentesis needle comprising a blunt-end needle and a stylet in the lumen of the needle. The stylet projects a short distance from the end of the needle on insertion and as soon as the needle is inserted the stylet is withdrawn from the needle.

U.S. Pat. No. 2,389,355 (Goland) issued Nov. 20, 1945, describes a needle for injecting fluids comprising a double cannula (inner and outer) with a rod in the inner cannula. The rod has no tissue piercing function, but rather serves as a means to prevent fluid from entering the cannula chamber.

U.S. Pat. No. 1,248,492 (Hill) issued Dec. 4, 1917, describes a cannula for withdrawing fluid comprising of a cannula/stylet combination wherein the cannula is slidably adjustable over the stylet.

U.S. Pat. No. 1,147,488 (Kells) issued Jul. 20, 1915, describes a needle having a sheath which surrounds the tissue at the point of puncture for the purpose of collecting any tissue fluids that may leak out around the puncture.

U.S. Pat. No. 3,628,524 (Jamshidi) issued Dec. 21, 1971, describes a biopsy needle having a stylet of substantially the same length situated inside the needle. The purpose of the stylet is to push the biopsy sample from the needle.

SUMMARY OF THE INVENTION

The present invention provides a needle having a sharp, pointed, beveled tip at its distal end and a lumen. The proximal end of the needle is affixed to a needle hub which can be of any configuration known in the art and which is capable of receiving a stylet and having a hollow-core inner compartment connecting the lumen of the needle with a syringe such that any fluid in the needle lumen can flow into the syringe upon applying suction or, vice versa, upon applying pressure.

The lumen of the needle is capable of receiving in a close-fitting relationship a stylet having a sharp, piercing, beveled tip. The distal piercing end of the stylet is inside the needle not extending beyond the distal tip of the needle when not in use. When the stylet is in use, the distal end of the stylet can extend beyond the distal end of the needle to any desired length, the preferred length being 2 to 6 mm and preferably 2 to 4 mm beyond the distal end of the needle. The distance the distal end of the stylet can extend beyond the distal end of the needle is controlled by the spacer mechanism.

BRIEF DESCRIPTION OF THE DRAWINGS

The present invention will be readily appreciated and better understood by reference to the following detailed description when considered in connection with the accompanying drawings wherein:

FIG. 2 is a side view of a needle and a stylet assembly having a removable slotted spacer mechanism.

FIG. 3 is a side view of a spacer mechanism which is a non-removable base of the stylet.

FIG. 4. shows the spacer mechanism of FIG. 3 engaging the needle flange.

FIG. 5. shows the spacer mechanism of FIG. 3 engaging the needle flange and moved downwardly.

DETAILED DESCRIPTION OF INVENTION

Figure 1:
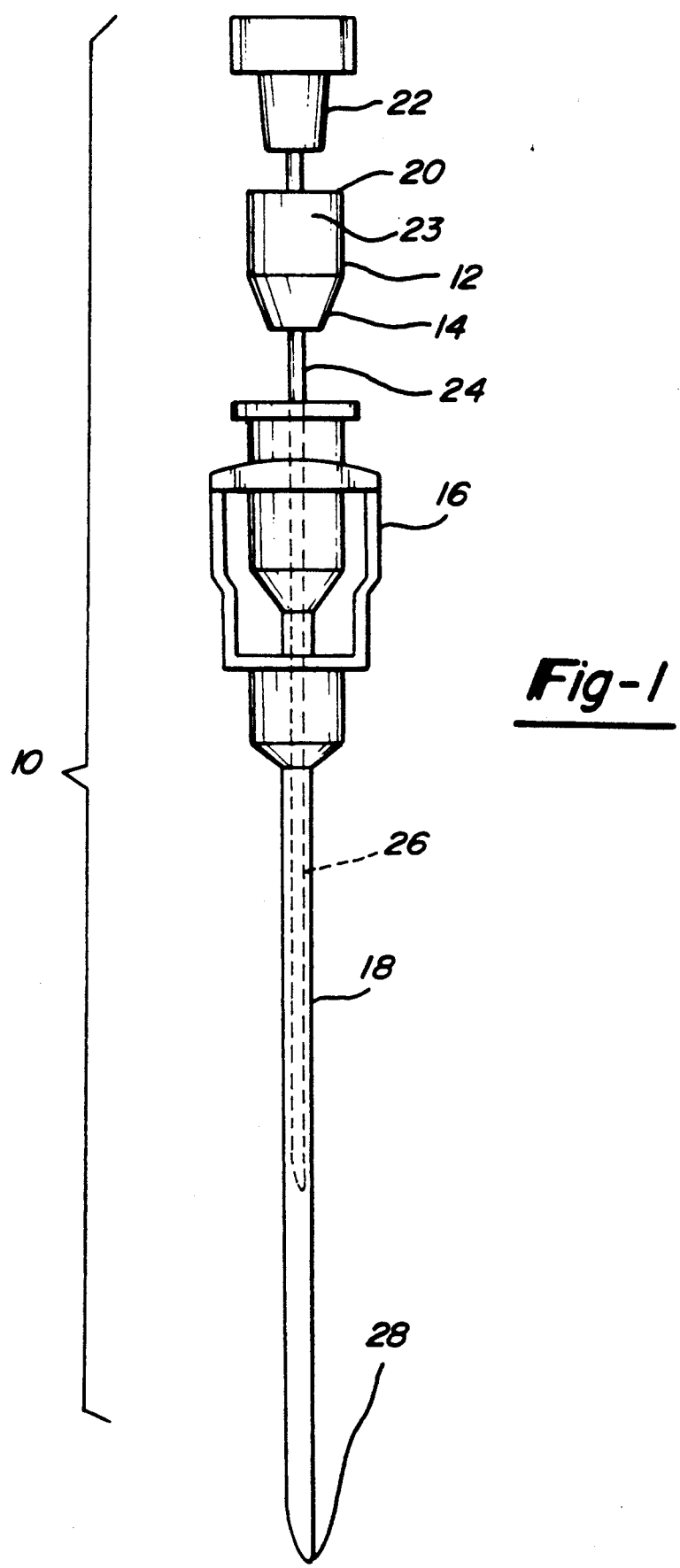
FIG. 1 is a side view of a needle and a stylet assembly having a removable non-slotted spacer mechanism.

The present invention is a modification of existing spinal needles. Early amniocentesis (those done at 14 weeks or earlier) are becoming more common. Problems with early amniocentesis is that it is frequently difficult to penetrate the membranes with a spinal needle such that there is tenting of the membranes without penetration by the needle. This results in a failed amniocentesis. Thrusting the needle forward can enter into the amniotic cavity but can also injure the developing fetus.

The invention claimed herein involves a stylet which can extend beyond the tip of the needle. With this modification, if tenting of the membranes is encountered the stylet is rapidly advanced and pierces the tented membranes. This then allows the needle to be advanced with resulting successful amniocentesis.

The preferred embodiment of this invention involves a spacer, which when in place, does not allow the stylet to advance beyond the tip of the needle. When the spacer is removed, the stylet can then advance a predetermined distance.

Although the needle assembly of the present invention is particularly useful in the performance of amniocentesis, other applications of the needle assembly will be readily apparent to those skilled in the art.

The spacer mechanism provides the basis of the present invention and can be of various configurations. The spacer mechanism serves to maintain the stylet within the lumen of the needle which can be considered a resting position until it is determined that the stylet should be extended beyond the distal tip of the needle to facilitate the operation intended to be achieved with the needle be it an extraction of fluid or tissue cells or an injection of fluid. To use the stylet feature of the needle assembly, the spacer assembly is either removed or the proximal end of the stylet is affixed in a base which can be rotated and locked into the hub of the needle in a manner as to project the distal end of the stylet beyond the distal end of the needle.

FIGS. 1-5 show various configurations for the spacer mechanism and needle assembly which are merely representative illustrations. Obviously, other configurations for the spacer mechanism could be devised. Primed numbers are used to indicate similar or corresponding elements of the different representative configurations.

FIGS. 1 and 2 show a needle assembly 10. FIG. 1 shows a removable spacer mechanism 12 having a distal portion 14 which can be seated in the hub 16 of the needle 18 when not in use and a proximal end 20 capable of receiving the stylet base 22 and a hollow center 23 such that when the needle assembly is not in use, the various pieces reside in essentially an interlocked position. Removal of the spacer mechanism is achieved by withdrawing the stylet 24 from the needle 18 and the spacer mechanism 12 and lifting the spacer mechanism 12 away from the needle hub 16 after which the stylet can be re-inserted into the needle 18. The distal end of the stylet base 22 is designed to fit snugly into the hub of the needle 16 and to permit the distal end of the stylet 26 to protrude beyond the distal end of the needle 28.

FIG. 2 shows another configuration for a removable spacer mechanism. The spacer mechanism 12 has a distal end 14' capable of snugly fitting into the needle hub 16' and has an opening or slot 30. The spacer mechanism has a hollow center 23' through which the stylet 24' can be inserted. To remove the spacer mechanism 12', it is withdrawn from the needle hub 16' and pulled away from the stylet 24' via the opening or slot 30. Upon removal of the spacer mechanism 12', the stylet 24' can be pushed downwardly into the needle with the base of the stylet 22' seating into the needle hub 16' and concurrently the distal end of the stylet projecting beyond the distal end of the needle.

FIGS. 3 to 5 show another configuration for the spacer mechanism, wherein the spacer mechanism 12" serves as a non-removable base of the stylet 24", having a proximal end 32 which can fit into or be affixed to a syringe (not shown) and a distal end 14" having flanges 34 which fit over the needle hub. When the stylet 24" is to be used, the base 12" is rotated 90° or 180° such that the flanges 34 of the stylet base 12" slip into slots 36 or grooves on the needle hub 16" permitting the distal end 14" of the spacer mechanism to be moved downwardly and concurrently moving the distal end of the stylet beyond the distal end of the needle.

The invention has been described in an illustrative manner and obviously many variations of the present invention are possible in view of the above teachings.

We claim:

1. A needle assembly which comprises:
    (1) a hollow needle open at each end and having a sharp, pointed, beveled distal tip for piercing a membrane;
    (2) a stylet having a sharp, pointed distal end; and
    (3) a spacer mechanism,
    (a) wherein the proximal end of the needle is affixed to a needle hub which has a hollow center for connecting the needle with a syringe and which is capable of receiving a stylet;
    (b) wherein the stylet is affixed to a base at its proximal end, wherein said base can be seated in the needle hub;
    (c) wherein the spacer mechanism is removably mounted over the stylet and between the needle hub and the base of the stylet in a manner such that the distal end of the stylet is contained within the hollow needle when the spacer mechanism is mounted and the stylet protrudes beyond distal end of the hollow needle 2 to 6 mm when the spacer mechanism is removed.

2. The needle assembly of claim 1, wherein the spacer mechanism has a tapered distal end capable of fitting into the needle hub.

3. The needle assembly of claim 2, wherein the spacer mechanism is a hollow tube-like structure having a slot extending from the proximal end to the distal end of the spacer mechanism and through which the stylet may pass.

4. A method of piercing a membrane by:
    seating a stylet within a hollow core of a needle while spacing a base of the stylet from a base of the needle to dispose the stylet completely within the hollow core of the needle, the spacing is defined by disposing a spacing member over the stylet and seated between the base of the stylet and the base of the needle;
    disposing an end of the needle against the membrane; and
    removing the spacing member between the base of the stylet and the base of the needle while plunging the stylet through the hollow core of the needle to extend the end of the stylet beyond the end of the needle with the end of the stylet then piercing the membrane.

* * * * *